(12) United States Patent
Jadhav et al.

(10) Patent No.: US 8,486,429 B2
(45) Date of Patent: *Jul. 16, 2013

(54) STORAGE STABLE FORMULATION AND A PROCESS FOR ITS PREPARATION

(75) Inventors: Prakash Mahadev Jadhav, Mumbai (IN); Jaidev Rajnikant Shroff, Mumbai (IN)

(73) Assignee: United Phosphorus, Ltd., Mumbai (IN)

( * ) Notice: Subject to any disclaimer, the term of this patent is extended or adjusted under 35 U.S.C. 154(b) by 1635 days.

This patent is subject to a terminal disclaimer.

(21) Appl. No.: 11/474,504

(22) Filed: Jun. 26, 2006

(65) Prior Publication Data

US 2006/0293287 A1    Dec. 28, 2006

Related U.S. Application Data

(60) Provisional application No. 60/694,246, filed on Jun. 28, 2005.

(51) Int. Cl.
| | |
|---|---|
| *A01N 25/00* | (2006.01) |
| *A61K 5/00* | (2006.01) |
| *A61K 9/28* | (2006.01) |
| *A61K 9/32* | (2006.01) |
| *A61M 36/14* | (2006.01) |

(52) U.S. Cl.
USPC ............ 424/405; 424/1.29; 424/474; 424/482

(58) Field of Classification Search
USPC ................... 424/405, 1.29, 474, 482
See application file for complete search history.

(56) References Cited

U.S. PATENT DOCUMENTS

| 5,476,833 A | 12/1995 | Fersch et al. |
| 5,560,909 A | 10/1996 | Rheaume et al. |
| 5,686,385 A * | 11/1997 | Akashi et al. ............ 504/359 |
| 5,750,130 A * | 5/1998 | Ferrell et al. ............ 424/417 |
| 6,391,336 B1 | 5/2002 | Royer |
| 6,497,901 B1 | 12/2002 | Royer |
| 6,682,751 B1 | 1/2004 | Hargrove et al. |
| 6,776,996 B2 | 8/2004 | Sun et al. |
| 7,445,791 B2 * | 11/2008 | Jadhav et al. ............ 424/421 |
| 2003/0194419 A1 * | 10/2003 | Sun et al. ............ 424/409 |
| 2003/0224031 A1 | 12/2003 | Heier et al. |

* cited by examiner

*Primary Examiner* — Mina Haghighatian
*Assistant Examiner* — Helen Chui
(74) *Attorney, Agent, or Firm* — Yancy IP Law, PLLC

(57) ABSTRACT

The present invention is directed to a storage stable insecticidal composition comprising one or more Chloronicotynyle compound, in an amount ranging from 0.1 to 5% by weight of the composition, one or more compounds falling within the group of Organophosphorus compounds in an amount ranging from 30 to 75% by weight of the composition and 69.9 to 20% by weight of conventional agriculturally acceptable carrier(s) and excepient(s) along with the process for obtaining the storage stable composition. At least one of the active ingredients is provided with a coating of a water soluble polymer.

12 Claims, No Drawings

US 8,486,429 B2

STORAGE STABLE FORMULATION AND A PROCESS FOR ITS PREPARATION

CROSS-REFERENCE TO RELATED APPLICATIONS

This application claims the benefit, under 35 U.S.C. 119 (e), of U.S. Provisional Application No. 60/694,246 filed Jun. 28, 2005, the contents of which are incorporated herein by reference.

BACKGROUND OF THE INVENTION

1. Field of the invention

This invention relates to an improved storage stable formulations. The invention particularly relates to an improved storage stable formulations of mutually incompatible active ingredients such as a Chloronicotynyle compound and an Organophosphorus compound. The invention more particularly relates to an improved storage stable formulation of mutually incompatible active ingredients such as Acephate and Imidacloprid. The present invention also relates to a process for the preparation of the above said storage stable formulation. The storage stable formulation of the present invention is useful for the protection of crops.

2. Description of Related Art

Enhancement of the agricultural produce requires the protection of the crops and its produce from pest damage. Various chemicals and their formulations have been developed and are in use currently for the effective management of the insect pests. Due to non-judicious use of the hitherto known pesticides, the pests gain resistance and it becomes difficult to kill them. The need for more food has to be met through higher yields per unit of the land, water, energy and time. Excessive use of mineral, fertilizers and chemical pesticides has caused soil degradation, ground water pollution and the spread of the pests resistant to pesticides in several areas. It, therefore, becomes necessary to have formulations of at least one or more pesticides formulated in such a way that they show an additional and/or better activity thereby exhibiting synergy.

Processes for preparing pesticidal agents and compositions have been developed to control pests. However, processes, which are economically efficient and provide ecologically safe pest control compositions, are still being sought. It is highly desirable to have a process for the preparation of pesticidal compositions, which allow for reduced effective dosage rates, increased environmental safety and lower incidence of pest resistance. Further, even though combinations of pest control agents have been studied, a high synergistic action has not always been found. Often, these mixtures show very low activity instead of the expected activity level either due to the intrinsic incompatibility of the active ingredients used and/or due to the product instability caused as a result of the incompatibility, thereby giving a shorter shelf life. In such cases, formulating these actives so as to achieve the best results of the combination poses a major hurdle.

A tank-mix of the two actives may or may not demonstrate synergy even if it is used in a certain manner by knowledgeable and skilled people under certain specific conditions. It is not pre-formulated and, therefore, can also prove to be a hazard during transport.

The above limitation may be overcome by providing a ready-to-use pre-formulated product. A pre-formulated product has many advantages including reduced handling, reduced risk of dosage error, reduced packaging, etc. However, this becomes difficult if the active ingredients used are unstable when mixed together.

This can be overcome by coating one of the actives by a barrier or a protective coat, which is the focus of the present invention.

One such example is that of Acephate and Imidacloprid, which are unstable when formulated together. Acephate is a systemic insecticide belonging to the phosphoroamidothioate class of compounds. It is used for control of a wide range of biting and sucking insects, especially aphids, including resistant species, in fruit, vegetables (e.g. potatoes and sugar beets), vine, and crop cultivation and in horticulture (e.g. on roses and chrysanthemums grown outdoors). It also controls leaf miners, lepidopterous larvae, sawflies and thrips in the previously stated crops as well as turf, mint and forestry. Acephate is unstable in alkaline pH and starts degrading.

Imidacloprid is a systemic, chloro-nicotinyl insecticide with soil, seed and foliar uses for the control of sucking insects including rice hoppers, aphids, thrips, whiteflies, termites, turf insects, soil insects and some beetles. It is most commonly used on rice, cereal, maize, potatoes, vegetables, sugar beets, fruit, cotton, hops and turf, and is especially systemic when used as a seed or soil treatment. The chemical works by interfering with the transmission of stimuli in the insect nervous system. Specifically, it causes a blockage in a type of neuronal pathway (nicotinergic) that is more abundant in insects than in warm-blooded animals (making the chemical selectively more toxic to insects than warm-blooded animals). This blockage leads to the accumulation of acetylcholine, an important neurotransmitter, resulting in the insect's paralysis, and eventually death. It is effective on and via stomach action. Imidacloprid is stable to hydrolysis at pH 5-11.

While Acephate is unstable in alkaline pH, Imidacloprid is unstable in acidic pH and it is difficult to formulate them together.

In the case of Acephate, since the rate of hydrolysis increases with increasing pH, degradation occurs more rapidly in alkaline soil than in acidic soil. Hence, it is necessary to protect the active from degradation to form its metabolites, which may or may not show any pesticidal activity and may be toxic. Therefore, it becomes necessary to formulate such incompatible actives in such a way as to enhance their synergistic property, making them storage stable compositions A process for preparing a coated pesticidal matrix, which protects the pesticidal activity of the active ingredient by coating it with a pH-dependent polymer already exists in the prior art.

A process also exists for making ingestible insecticide compositions comprising entrapping the insecticide in a suitably charged polymer in aqueous medium, then modifying the charge of the polymer to cause precipitation of the polymer thereby entrapping the insecticide in it.

However, synthetic or non-biodegradable polymers pose a problem to the environment and are therefore, not preferred. Naturally occurring polymers are better suited for this purpose and have been used in various controlled release formulations.

Pesticide granules, which were prepared by blending the pesticide with solid carriers and extruded are also known. The extruded granules were then coated with a solution of binder and optionally with a solution of a dispersant and finally dried.

Inorganic polymer complexes for controlled release of compounds comprising a hydrated or crystallized inorganic compound and a matrix polymer which slows down the release of the active agent also are known.

The production and use of inorganic-conditioning agent complexes comprising of resorbable matrices formed by mixing an inorganic compound capable of undergoing hydration and/or crystallization, a conditioning agent that improves stability, a matrix polymer and/or a complexing agent are also known. The system can be used for controlled release of actives.

Water dispersible, dry, flowable granules of agricultural chemicals, such as quinclorac, which are coated with a water-soluble coating layer of polyvinyl alcohol are known. The granules are formulated to reduce or eliminate any chemical residue on interior surfaces of containers used to package the formulations for transport/handling thereby enhancing the safety. The drawback of using polyvinyl alcohol is that it has a high melting point and hence the reaction will involve high temperatures at which active ingredients like Acephate will degrade. So, this polymer is unsuitable for active ingredients that are heat-unstable. Besides this, the process of coating is carried out by dissolving polyvinyl alcohol in water. This makes it unsuitable for using with active ingredients that are moisture-sensitive. Acephate is also sensitive to moisture and degrades rapidly, so this method is not advisable for compositions containing Acephate.

Other polymers, which are not water-soluble, have limitations and in compositions where one of the active ingredients is soluble in the organic solvent used for dissolving the polymer, the release of such active would pose a problem.

BRIEF SUMMARY OF THE INVENTION

Accordingly, the present invention provides an improved storage stable formulation useful for the protection of crops comprising active ingredients which are not compatible such as a Chloronicotynyle compound and an Organophosphorus compound wherein at least one of the active ingredients are provided with a coating of a water soluble polymer.

According to still another embodiment of the present invention there is provided an improved storage stable formulation useful for the protection of crops comprising active ingredients which are not compatible such as Imidacloprid and Acephate wherein at least one of the active ingredients are provided with a coating of a water soluble polymer.

According to another embodiment of the present invention there is provided an improved storage stable formulation useful for the protection of crops comprising active ingredients which are not compatible which comprises (i) Imidacloprid in an amount in the range of 0.1 to 25 wt %, (ii) Acephate in an amount in the range of 5 to 97 wt %, at least one of the active agents being coated with a low-melting, water-soluble polymer which is thermostable, in an amount in the range of 0.08 to 50 wt %, (iii) wetting agents in an amount in the range of 0.1 to 2.0 wt %, (iv) dispersing agent/s in an amount in the range of 0.5 to 7.0 wt % (v), stabilizers in an amount in the range of 0.1 to 3.0 wt % and (vi) inert fillers in an amount in the range of 10 to 50 wt %.

According to another embodiment of the present invention there is provided a process for the preparation of an improved storage stable formulation useful for the protection of crops comprising as active ingredients which are not compatible such as a Chloronicotynyle compound and an Organophosphorus which comprises coating the crystalline solid particles of at least one of the active ingredients with a melted form of a water soluble coating material and then blending the rest of the essential components to form a homogenous mixture in powder form and if desired converting the powder into granules or pellets by conventional methods.

According to another embodiment of the present invention there is a provided a process for the preparation of an improved storage stable formulation useful for the protection of crops comprising as active ingredients which are not compatible such as Imidacloprid and Acephate which comprises coating the crystalline solid particles of each of the active ingredients with a water soluble coating material in melt form and then blending the individual melts to form a homogenous mixture in powder form and if desired converting.

The present invention provides an improved storage stable formulation of mutually incompatible active ingredients such as Chloronicotynyle compound and an Organophosphorus compound which is useful for the protection of crops.

The present invention provides an improved storage stable formulation of mutually incompatible active ingredients such as Imidacloprid and Acephate which is useful for the protection of crops.

The present invention provides an improved storage stable formulation containing Imidacloprid & Acephate from degradation if exposed to moisture which is useful for the protection of crops.

The present invention provides a process for the preparation of an improved storage stable formulation containing mutually incompatible active ingredients such as a Chloronicotynyle compound and an Organophosphorus compound which is useful for the protection of crops.

The present invention provides a process for the preparation of an improved storage stable formulation containing mutually incompatible active ingredients such as Imidacloprid and Acephate which is useful for the protection of crops The above mentioned invention is achieved by providing a barrier between the mutually incompatible agents, which are in solid form, such as a Chloronicotynyle compound and an Organophosphorus compound, more preferably an Imidacloprid and Acephate.

DETAILED DESCRIPTION OF THE INVENTION

The present invention provides a storage stable synergistic insecticidal composition containing a Chloronicotynyle compound and an Organophosphorus compound. A synergistically effective amount of one or more compounds falling within a group of Chloronicotynyle compounds is preferably ranging from 0.1 to 5% by weight of the composition, more preferably in the range of 0.5 to 3.0%. The Chloronicotynyle compounds are preferably selected from the group consisting of Imidacloprid and Acetamiprid, most preferably Imidacloprid, which may be technical grade and provided in a purity of 95% minimum. The Chloronicotynyle compound is provided in combination with one or more Organophosphorus compounds present in an amount preferably ranging from 30 to 75% by weight of the composition, more preferably 35 to 60%. The compounds falling under the group of Organophosphorus compounds are preferably selected from the group consisting of Acephate and Phosphamidon, more preferably Technical grade Acephate having a purity of 97% minimum and technical grade Phosphamidon having a purity of 92% minimum. The synergistic insecticidal composition also preferably includes 0.08-50% by weight of a composition which is a low-melting, thermostable, water-soluble polymer along with conventional agriculturally acceptable carrier(s) and/or excipients.

The name "Acetamiprid" describes a chemical substance having a molecular weight 222.7; is in the form of colourless crystals, m.pt. 98.9° C.; solubility in water at 25° C., 4200 mg/l. soluble in acetone, methanol, ethanol, dichloromethane, chloroform, acetonitrile and tetrahydrofuron. Stable in buffered solutions at pH 4, 5, 7. Degraded slowly at pH 9 and 45° C. Stable under sunlight. The molecule have following formula: (E)-N'-[(6-chloro-3-pyridyl)methyl]-N- cyano-N-methylac-etamidine. It is a systemic insecticide for soil and foliar application. It controls Hemiptera, especially aphids, Thysanoptera and Lepidoptera on a wide range of crops, especially vegetables, fruits and tea. Its acute oral LD50 for male rats 217, female rats 146, male mice 198, female mice 184 mg/Kg. Acute percutaneous LD50 for male and female rats >2000 mg/Kg. Non irritating to skin and eyes (rabbits) During inhalation LC50 (4 h) for male and female rats is about >0.29 mg/l.

The name "Imidacloprid" describes a chemical substance having a molecular weight 255.7; is in the form of colourless crystals with a weak characteristic odour, m.pt. 144° C.; solubility in water at 20° C., 0.61 g/l. In dichloromethane 55, isopropanol 1.2, toluene 0.68, n.hexane <0.1 (all in g/l. 20° C.). Stable to hydrolysis at pH 5-11. The molecule has the following formula: 1-(6-chloro-3-pyridylmet-hyl)-N-nitroimidazolidin-2-yldeneamine. It acts on the central nervous system, causing blockage of postsynaptic nicotinergic acetylcholine receptors. It is a systemic insecticide with contact and stomach action. Readily taken up by the plant and further distributed acropetally, with good root-systemic action. It controls the sucking insects, including rice-hoppers, aphids, thrips and whiteflies. Also effective against soil insects, termites and some species of biting insects, such as rice water weevil and Colorado beetle. It has no effect on nematodes and spider mites. Used as seed dressing, as soil treatment and as foliar treatment in different crops, e.g. rice, cotton, cereals maize sugar beet, potatoes, vegetables citrus fruit, pome fruit and stone fruit. Its acute oral LD50 for male and female rats 450, mice 150 mg/Kg. Acute percutaneous LD50 (24 h) for rats >5000 mg/Kg. Non irritating to skin and eyes (rabbits). Not a skin sensitiser. During inhalation LC50 (4 h) for female rats is >5323 mg/m.sup.3 air (aerosol). Not mutagenic or teratogenic.

The Organophosphorus compounds have high insecticidal and acaricidal activity; have wide spectrum of the action on plant pests; low persistence and breakdown to form products nontoxic to human and animals; systemic action of a number of the compounds; low dosage of the compound per unit area treated; relatively rapid metabolism in vertebrate organism and absence of accumulation in their bodies, and also comparatively low chronic toxicity; rapidity of action on plant pests. The preferred compounds for use as Organophosphorus compounds are Acephate and Phosphamidon.

"Acephate" (O,S-dimethylacetylphosphoramidothioate) belongs to the Organophosphorus group and has the structural formula as follows: (O,S-dimethylacetylphosphoramidothioate). It is a cholinesterase inhibitor. It is a systemic insecticide with contact and stomach action and is of moderate persistence with residual activity lasting about 10-21 days. It controls a wide range of chewing and sucking insects, e.g. aphids, thrips, lepidopterous larvae, sawflies, leaf miners, leafhloppers, cutworms, etc. in fruits (including citrus), vines, hops, olives, cotton soyabean, peanuts, macadamia nuts, beet, brassicas, celery, beans, potatoes, rice, tobacco ornamentals, forestry, and other crops. It is non-phytotoxic to most crop plants but marginal leaf bum may occur on Red Delicious apples. Technical grade Acephate is >97% pure. It has a molecular weight of 183.2 is a colourless solid; melting point 88-90° C.; solubility at room temperature: about 790 g/l water (20 C); 151 acetone, >100 ethanol; 35 ethyl acetate, 16 benzene, 0.1 hexane (all in g/l, 20° C.). Relatively stable to hydrolysis; DT50 40° C. 60 h (pH 9), 710 h (pH 3).

The "Phosphamidon" as a commercial compound contains 70% m/m (Z)-isomer (β-isomer) (which has the greater insecticidal activity) and 30% m/m (E)-isomer (α-isomer). Phosphamidon is a systemic insecticide and acaricide with stomach and slight contact action. It is a pale yellow/brown liquid with the molecular structure as follows: 2-chloro-2-diethyl-carbamoyl-1-methylvinyldimethylphosphate. It is absorbed by the leaves and roots. It is cholinesterase inhibitor. It is used in control of sucking, chewing and boring insects, and spider mites on a very wide range of crops. Specifically used in control of leaf beetles and stem borers in rice; stem borers in sugarcane; colarado beetles in potatoes; thrips in cotton; etc. It is also used to control aphids, sawflies, suckers, fruit flies, leaf miners, moth and beetle larvae, and many other insects in fruits, vines, olives, vegetables, ornamentals, cereals, beet, maize, alfalfa, many other crops and in forestry. It is non-phytotoxic, except some varieties of cherry, plum, peach and sorghum. It is compatible with many other pesticides, but incompatible with alkaline materials. It has a boiling point 162° C. (at 1.5 mm Hg); Solubility-miscible with water, acetone, dichloromethane, toluene and other common organic solvents, with the exception of aliphatic hydrocarbons e.g. solubility in hexane 32 g/l (25° C.). It gets rapidly hydrolysed in alkali: DT 50 (calculated) (20° C.) 60 d (pH 5); 54 d (pH 7); 12 d (pH 9). Its acute oral LD 50 for rats 17.9-30 mg/Kg. Acute percutaneous LD 50 for rats 374-530, rabbits 267 mg/Kg. Slight skin irritation, moderate eye irritation in rabbits observed. During inhalation LC 50 (4 h) for rats is about 0.18, mice 0.033 mg/l air. In mammals, following oral administration, 85-90% of the dose is excreted within 24 hours, almost entirely in the urine. Complete metabolism occurs during the passage, by oxidative dealkylation of the amide group and hydrolysis of the phosphorus ester bond. In plants, an ethyl group is split off from the amide group and simultaneously or subsequently the ester bond between the side chain and phosphorus atom is hydrolytically cleaved. De-chlorination also occurs, as does further degradation to small fragments.

The coating agent in the present invention include cyclodextrins, water soluble polymers and/or water insoluble polymers; preferably water soluble polymers like PEG 400, PEG 4000, PEG 6000, PEG 8000 and PEG 10000, polyvinyl alcohol, polyethylene oxide, polyacrylamide, sodium polyacrylate, polyvinyl pyrollidone, copolymer of methyl methacrylate, butyl methacrylate and dimethylaminoethyl methacrylate (Eudragit RTM.), polycaprolactam.

Evaluation of the synergistic insecticidal effect of the Chloronicotynyle compound, for example Imidacloprid, plus a second insecticide Organophosphorus compound, for example Acephate or Phosphamidon, can be established by using any synergistic insecticidal composition.

Synergism can be calculated by using the Colby's method i.e. the expected (or predicted) response of the combination is calculated by taking the product of the observed response for each individual component of the combination when applied alone divided by 100 and subtracting this value from the sum of observed response for each component when applied alone. Synergism of the combination is then determined by comparing the observed response of the combination to the expected (or predicted) response as calculated from the observed response of each individual component alone. If the observed response of the combination is greater than the expected (or predicted) response then the combination is said to be synergistic and falls within the definition of synergistic effect. (Colby, S. R., Weeds, 1967(15), p. 20-22)

TABLE A

Synergistic insecticidal effect of a combination of Imidacloprid + Acephate

| S. No. | Imidacloprid (ppm) | Acephate (ppm) | Observed Mortality % | Expected Mortality % | Difference |
|---|---|---|---|---|---|
| 1 | 24 | 0 | 55.00 | — | — |
| 2 | 27 | 0 | 69.25 | — | — |
| 3 | 30 | 0 | 72.10 | — | — |
| 4 | 0 | 600 | 52.50 | — | — |
| 5 | 0 | 700 | 60.00 | — | — |
| 6 | 0 | 800 | 70.00 | — | — |
| 7 | 24 | 600 | 70.00 | 78.63 | −8.63 |
| 8 | 24 | 700 | 71.75 | 82.00 | −10.25 |
| 9 | 24 | 800 | 93.00 | 86.50 | 6.50 |
| 10 | 27 | 600 | 88.8 | 85.40 | 2.60 |
| 11 | 27 | 700 | 91.00 | 87.70 | 3.30 |
| 12 | 27 | 800 | 97.05 | 90.78 | 6.27 |
| 13 | 30 | 600 | 90.00 | 86.75 | 3.25 |
| 14 | 30 | 700 | 95.00 | 88.84 | 6.16 |
| 15 | 30 | 800 | 99.5 | 91.63 | 7.87 |

As can be seen from the data shown in Table 1, combinations of Imidacloprid plus a organophosphorus compound, for example Acephate, demonstrate synergistic insect control.

However the synergistic effect has to be evaluated in relation to the storage stability of the combination product. It has been found that the active ingredients undergo degradation under certain conditions.

The following experiment details are provided to illustrate the synergistic nature of the present invention. However, the present invention is not intended to be limited to these specific examples. One of ordinary skill in the art will appreciate that variation of the examples presented could lead to the desired synergistic outcome of the present invention.

Experiment 1

Acephate technical of 97.5% purity was taken and kept in AHS stability study at 30, 45 and 54° C. in trilaminated pouches. The results of the AHS experiment for Acephate Technical are seen in the following Tables 1, 2 and 3.

TABLE 1

Stability of Acephate Technical at 30° C.

| Expt. No. | pH of 1% aq. Solution (Initial) | pH of 1% aq. Solution (14 days AHS) | % Acephate at ambient Initial | % Acephate at 30° C. after 14 days | % Acephate Degraded at 30° C. |
|---|---|---|---|---|---|
| 1 | 4.70 | 4.58 | 97.5 | 97.5 | NIL |

TABLE 2

Stability of Acephate Technical at 45° C.

| Expt. No. | pH of 1% aq. Solution (Initial) | pH of 1% aq. Solution (14 days AHS) | % Acephate at ambient Initial | % Acephate at 45° C. after 14 days | % Acephate Degraded at 45° C. |
|---|---|---|---|---|---|
| 1 | 4.70 | 4.58 | 97.5 | 97.5 | NIL |

TABLE 3

Stability of Acephate Technical at 54° C.

| Expt. No. | pH of 1% aq. Solution (Initial) | pH of 1% aq. Solution (14 days AHS) | % Acephate at ambient (Initial) | % Acephate at 54° C. 14 days | % Acephate degraded at 54° C. in 14 days |
|---|---|---|---|---|---|
| 1 | 4.70 | 4.58 | 97.5 | 95.98 | 1.56 |

The above Tables 1, 2 and 3 indicate that active content of Acephate technical and the pH does not change significantly during the stability studies conducted at 30° C., 45° C. and 54° C. for 14 days wherein the initial pH is 4.70. However, when the Acephate 97.5% mixed with citric acid in different ratios resulting in different initial pH of the formulation was subjected to stability studies, it was found to degrade as shown in following examples:

Experiment 2

40 gm Acephate technical of 97.5% purity was taken from plant and mixed with 10 gm of citric acid by using laboratory made mixture to obtained homogenious powder and is then kept in AHS at 30, 45 and 54° C. in trilaminated pouches.

Experiment 3

40 gm Acephate technical of 97.5% purity was taken from plant and mixed with 5 gm of citric acid by using laboratory made mixture to obtained homogenious powder and is the kept in AHS at 30, 45 and 54° C. in trilaminated pouches.

Experiment 4

48 gm Acephate technical of 97.5% purity was taken from plant and mixed with 2 gm of citric acid by using laboratory made mixture to obtained homogenious powder and is the kept in AHS at 30, 45 and 54° C. in trilaminated pouches.

The results of the experiments are shown in Tables 4, 5 and 6 below:

TABLE 4

Stability of Acephate technical 97.5% with citric acid in different ratios at 30° C.

| Expt. No. | pH 1% aq. Suspension (Initial) | pH 1% aq. Suspension (14 days AHS1) | % Acephate ambient Initial | % Acephate 30° C. 14 days | % Acephate. Degradation 30° C. |
|---|---|---|---|---|---|
| 2 | 2.80 | 1.8 | 78.00 | 61.191 | 21.55 |
| 3 | 3.2 | 2.55 | 86.66 | 77.898 | 10.11 |
| 4 | 3.89 | 3.58 | 93.6 | 93.132 | 0.50 |

TABLE 5

Stability of Acephate technical 97.5% with citric acid in different ratios at 45° C.

| Expt. No. | pH 1% aq. Suspension (Initial) | pH 1% aq. Suspension (14 days AHS1) | % Acephate ambient Initial | % Acephate 45° C. 14 days | % Acephate. Degradation 45° C. |
|---|---|---|---|---|---|
| 2 | 2.80 | 1.8 | 78.00 | 60.16 | 22.87 |
| 3 | 3.2 | 2.55 | 86.66 | 75.58 | 12.79 |
| 4 | 3.89 | 3.58 | 93.6 | 92.77 | 0.89 |

TABLE 6

Stability of Acephate technical 97.5% with citric acid in different ratios at 54° C.

| Expt. No. | pH 1% aq. Suspension (Initial) | pH 1% aq. Suspension (14 days AHS1) | % Acephate. ambient | % Acephate 54° C. 14 days | % Acephate degradation 54° C. 14 days |
|---|---|---|---|---|---|
| 2 | 2.80 | 1.8 | 78.00 | 17.06 | 78.13 |
| 3 | 3.2 | 2.55 | 86.66 | 67.20 | 22.46 |
| 4 | 3.89 | 3.58 | 93.6 | 92.308 | 1.38 |

The above experiments show that the degradation of Acephate is least at a pH of 3.89 when Acephate technical and citric acid are mixed in a ratio of 48:2. It also shows that the degradation of Acephate mixed with citric acid further increases with the increase in temperature.

The degradation of Acephate is higher at a lower pH of 3.2 wherein the Acephate technical and citric acid are mixed in a ratio of 40:5. It also shows that the degradation of Acephate mixed with citric acid further increases with the increase in the temperature.

The degradation of Acephate is maximum at a pH of 2.80 when Acephate technical and citric acid are in a ratio of 40:10. It also shows that the degradation of Acephate mixed with citric acid still further increases with the increase in the temperature.

Thus the Acephate is shown to degrade as the pH decreases from the pH 3.89 to pH 2.80. Acephate mixed with citric acid is also shown to degrade at a higher temperature.

Acephate is also shown to degrade to a large extent at a higher temperature and lower pH. Thus Acephate is shown to degrade under conditions of
  a. Higher Temperature
  b. Lower pH than 3.89
It has also been found that Moisture has been responsible for the degradation of Acephate.

Experiment 5

Acephate technical of 97.5% purity was taken from the plant and mixed in a laboratory mixer by adding 1% water and was then kept in AHS stability study at 30° C., 45° C. and 54° C. in trilaminated pouches.

TABLE 7

Stability of Acephate with 1% water at 30° C.

| Expt. No. | pH of 1% aq. Suspension (Initial) | pH of 1% aq. Suspension (14 days AHS1) | % a.i. Ambient (Initial) | % a.i 30° C. 14 days | % a.i. Degradation 30° C. |
|---|---|---|---|---|---|
| 1 | 4.70 | 4.58 | 97.5 | 97.5 | Nil |
| 5 | 4.68 | 2.58 | 96.80 | 88.88 | 8.18 |

TABLE 8

Stability of Acephate with 1% water at 45° C.

| Expt. No. | pH of 1% aq. Suspension (Initial) | pH of 1% aq. Suspension (14 days AHS1) | % a.i. Ambient (Initial) | % a.i 45° C. 14 days | % a.i. Degradation 45° C. |
|---|---|---|---|---|---|
| 1 | 4.70 | 4.58 | 97.5 | 97.5 | — |
| 5 | 4.68 | 2.58 | 96.80 | 86.19 | 10.96 |

TABLE 9

Stability of Acephate with 1% water at 54° C.

| Expt. No. | PH 1% aq. Suspension (Initial) | pH 1% aq. Suspension (14 days AHS) | % a.i. Ambient Initial | % a.i 54° C. 14 days | % a.i degradation 54° C. 14 days |
|---|---|---|---|---|---|
| 1 | 4.70 | 4.58 | 97.5 | 95.98 | 1.56 |
| 5 | 4.68 | 2.58 | 96.80 | 84.80 | 12.4 |

The above experiments show that the degradation of Acephate is more in the presence of moisture. It also shows that the degradation of Acephate increases with the increase in the temperature.

Acephate is also shown to degrade more at a higher temperature and in presence of moisture.

Thus Acephate is shown to degrade under conditions of
a. Higher Temperature
b. Lower pH than 3.89
c. Presence of Moisture However it has been found that Acephate degrades at a pH of 3.89 due to the presence of citric acid and moisture to a lower extent than the degradation with moisture in the absence of citric acid.

Experiment 6

Acephate technical of 97.5% purity was taken from the plant and mixed in laboratory mixer by adding 1% water 4% citric acid and was then kept in AHS stability study at 30, 45 and 54° C. in trilaminated pouches.

TABLE 10

Stability of Acephate mixed 4% Citric acid and with 1% water at 30° C.

| Expt. No. | pH 1% aq. Suspension (Initial) | pH 1% aq. Suspension (14 days AHS) | % a.i. Ambient Initial | % a.i 30° C. 14 days | % a.i. Degradation 30° C. |
|---|---|---|---|---|---|
| 1 | 4.70 | 4.58 | 97.5 | 95.98 | 1.56 |
| 6 | 3.18 | 2.10 | 95.21 | 91.25 | 4.16 |

TABLE 11

Stability of Acephate mixed 4% Citric acid and with 1% water at 45° C.

| Expt. No. | pH 1% aq. Suspension (Initial) | pH 1% aq. Suspension (14 days AHS) | % a.i. Ambient Initial | % a.i 45° C. 14 days | % a.i. Degradation 45° C. |
|---|---|---|---|---|---|
| 1 | 4.70 | 4.58 | 97.5 | 95.98 | 1.56 |
| 6 | 3.18 | 2.10 | 95.21 | 89.68 | 5.81 |

TABLE 12

Stability of Acephate mixed 4% Citric acid and with 1% water at 54° C.

| Expt. No. | pH 1% aq. Suspension (Initial) | pH 1% aq. Suspension (14 days AHS) | % a.i. Ambient Initial | % a.i 54° C. 14 days | % a.i degradation 54° C. 14 days |
|---|---|---|---|---|---|
| 1 | 4.70 | 4.58 | 97.5 | 95.98 | 1.56 |
| 6 | 3.18 | 2.10 | 95.21 | 88.65 | 6.89 |

Conclusion

The results in the above tables show that although the presence of 1% moisture degrades Acephate to an extent of 12.84% at 54° C. at the initial pH of 4.70 due to the absence of Citric acid, whereas Acephate degrades by 6.88% at 54° C. when the initial pH is 3.18 due to presence of Citric acid and 1% moisture.

The present invention also involves the use of Imidacloprid as another component of the composition. Imidacloprid shows degradation in the presence of moisture and at a higher temperature and at a low pH Experiment 7

Imidacloprid technical was taken from the plant and is kept in AHS stability study at 30, 45 and 54° C. in trilaminated pouches.

TABLE 13

Stability of Imidacloprid at 30° C.

| Expt. No. | pH 1% aq. Suspension (Initial) | pH 1% aq. Suspension (14 days AHS) | % Imida ambient | % imida at 30° C. 14 days | % imida Degradation at 30° C. 14 days |
|---|---|---|---|---|---|
| 7 | 5.9 | 5.88 | 98.26 | 98.26 | NIL |

TABLE 14

Stability of Imidacloprid at 45° C.

| Expt. No. | pH 1% aq. Suspension (Initial) | pH 1% aq. Suspension (14 days AHS) | % Imida ambient | % imida at 45° C. 14 days | % imida Degradation at 45° C. 14 days |
|---|---|---|---|---|---|
| 7 | 5.9 | 5.88 | 98.26 | 97.14 | 1.14 |

TABLE 15

Stability of Imidacloprid at 54° C.

| Expt. No. | pH 1% aq. Suspension (Initial) | pH 1% aq. Suspension (14 days AHS) | % Imida ambient | % imida at 54° C. 14 days | % imida Degradation at 54° C. 14 days |
|---|---|---|---|---|---|
| 7 | 5.9 | 5.88 | 98.26 | 97.08 | 1.20 |

Experiment 8

Imidacloprid technical was taken from the plant and mixed in laboratory mixer by adding 1% water and is then is kept in AHS stability study at 45 and 54° C. in trilaminated pouches.

TABLE 16

Stability of Imidacloprid with 1% water at 30° C.

| Expt. No. | pH 1% aq. Suspension (Initial) | pH 1% aq. Suspension (14 days AHS) | % Imida ambient Initial | % imida at 30° C. 14 days | % imida Degradation at 30° C. 14 days |
|---|---|---|---|---|---|
| 8 | 5.91 | 5.85 | 96.15 | 94.77 | 1.44 |

TABLE 17

Stability of Imidacloprid with 1% water at 45° C.

| Expt. No. | pH 1% aq. Suspension (Initial) | pH 1% aq. Suspension (14 days AHS) | % Imida ambient | % imida at 45° C. 14 days | % imida Degradation at 45° C. 14 days |
|---|---|---|---|---|---|
| 8 | 5.91 | 5.85 | 96.15 | 94.33 | 1.89 |

TABLE 18

Stability of Imidacloprid with 1% water at 54° C.

| Expt. No. | pH 1% aq. Suspension (Initial) | pH 1% aq. Suspension (14 days AHS) | % Imida ambient Initial | % imida at 54° C. 14 days | % imida degradation at 54° C. 14 days |
|---|---|---|---|---|---|
| 8 | 5.91 | 5.85 | 96.15 | 94.28 | 1.95 |

The above experiment 8 and tables 16, 17 and 18 show that Imidacloprid degrades to some extent in the presence of moisture Similarly since it is shown that Acephate shows some stability in presence of Citric acid, the stability of Imiacloprid in the presence of Citric acid is also checked.

Experiment 9

40 gm of Imidacloprid technical and 10 gm of citric acid was mixed in laboratory mixer and was then kept in AHS stability study at 30, 45 and 54° C. in trilaminated pouches,

TABLE 19

Stability of Imidacloprid(40 gms) mixed with citric acid(10 gms) at 30° C.

| Expt. No. | pH 1% aq. Suspension (Initial) | pH 1% aq. Suspension (14 days AHS) | % Imida ambient Initial | % imida at 30° C. 14 days | % imida degradation at 30° C. 14 days |
|---|---|---|---|---|---|
| 9 | 2.68 | 3.58 | 75.10 | 31.31 | 58.31 |

TABLE 20

Stability of Imidacloprid(40 gms) mixed with citric acid(10 gms) 45° C.

| Expt. No. | pH 1% aq. Suspension (Initial) | pH 1% aq. Suspension (14 days AHS) | % Imida ambient Initial | % imida at 45° C. 14 days | % imida degradation at 45° C. 14 days |
|---|---|---|---|---|---|
| 9 | 2.68 | 4.13 | 75.10 | 28.42 | 62.16 |

TABLE 21

Stability of Imidacloprid(40 gms) mixed with citric acid(10 gms) at 54° C.

| Expt. No. | pH 1% aq. Suspension (Initial) | pH 1% aq. Suspension (14 days AHS) | % Imida ambient Initial | % imida at 54° C. 14 days | % imida degradation at 54° C. 14 days |
|---|---|---|---|---|---|
| 9 | 2.68 | 4.58 | 75.10 | 24.93 | 66.80 |

Experiment 10

45 gm of Imidacloprid technical and 05 gm of citric acid was mixed in laboratory mixer and was then kept in AHS stability study at 30° C., 45° C. and 54° C. in trilaminated pouches.

TABLE 22

Stability of Imidacloprid(45 gms) mixed with citric acid(5 gms) at 30° C.

| Expt. No. | pH 1% aq. Suspension (Initial) | pH 1% aq. Suspension (14 days AHS) | % Imida ambient Initial | % imida at 30° C. 14 days | % imida degradation at 30° C. 14 days |
|---|---|---|---|---|---|
| 10 | 2.84 | 3.46 | 76.98 | 44.64 | 42.01 |

TABLE 23

Stability of Imidacloprid(45 gms) mixed with citric acid(5 gms) at 45° C.

| Expt. No. | pH 1% aq. Suspension (Initial) | pH 1% aq. Suspension (14 days AHS) | % Imida ambient Initial | % imida at 45° C. 14 days | % imida degradation at 45° C. 14 days |
|---|---|---|---|---|---|
| 10 | 2.84 | 3.78 | 76.98 | 38.24 | 47.88 |

TABLE 24

Stability of Imidacloprid(45 gms) mixed with citric acid(5 gms) at 54° C.

| Expt. No. | pH 1% aq. Suspension (Initial) | pH 1% aq. Suspension (14 days AHS) | % Imida ambient Initial | % imida at 54° C. 14 days | % imida degradation at 54° C. 14 days |
|---|---|---|---|---|---|
| 10 | 2.84 | 4.10 | 76.98 | 37.04 | 50.32 |

Experiment 11

48 gm of Imidacloprid technical and 2 gm of citric acid was mixed in laboratory mixer and was then kept in AHS stability study at 30, 45 and 54° C. in trilaminated pouches.

TABLE 25

Stability of Imidacloprid(48 gms) mixed with citric acid(2 gms) at 30° C.

| Expt. No. | pH 1% aq. Suspension (Initial) | pH 1% aq. Suspension (14 days AHS) | % Imida ambient Initial | % imida at 30° C. 14 days | % imida degradation at 30° C. 14 days |
|---|---|---|---|---|---|
| 11 | 3.14 | 3.48 | 77.14 | 50.00 | 35.18 |

TABLE 26

Stability of Imidacloprid(48 gms) mixed with citric acid(2 gms) at 45° C.

| Expt. No. | pH 1% aq. Suspension (Initial) | pH 1% aq. Suspension (14 days AHS) | % Imida ambient Initial | % imida at 45° C. 14 days | % imida degradation at 45° C. 14 days |
|---|---|---|---|---|---|
| 11 | 3.14 | 3.78 | 77.14 | 47.33 | 38.64 |

TABLE 27

Stability of Imidacloprid(48 gms) mixed with citric acid(2 gms) at 54° C.

| Expt. No. | pH 1% aq. Suspension (Initial) | pH 1% aq. Suspension (14 days AHS) | % Imida ambient Initial | % imida at 54° C. 14 days | % imida degradation at 54° C. 14 days |
|---|---|---|---|---|---|
| 11 | 3.14 | 3.80 | 77.14 | 46.53 | 39.68 |

Experiment 12

49.5 gm of Imidacloprid technical and 0.5 gm of citric acid was mixed in laboratory mixer and was then kept in AHS stability study at 30, 45 and 54° C. in trilaminated pouches.

TABLE 28

Stability of Imidacloprid(49.5 gms) mixed with citric acid(0.5 gms) at 30° C.

| Expt. No. | pH 1% aq. Suspension (Initial) | pH 1% aq. Suspension (14 days AHS) | % Imida ambient Initial | % imida at 30° C. 14 days | % imida degradation at 30° C. 14 days |
|---|---|---|---|---|---|
| 11 | 3.60 | 3.85 | 77.82 | 63.70 | 18.14 |

TABLE 29

Stability of Imidacloprid(49.5 gms) mixed with citric acid(0.5 gms) at 45° C.

| Expt. No. | pH 1% aq. Suspension (Initial) | pH 1% aq. Suspension (14 days AHS) | % Imida ambient Initial | % imida at 45° C. 14 days | % imida degradation at 45° C. 14 days |
|---|---|---|---|---|---|
| 12 | 3.60 | 3.98 | 77.82 | 60.34 | 22.46 |

TABLE 30

Stability of Imidacloprid (49.5 gms) mixed with citric acid (0.5 gms) at 54° C.

| Expt. No. | pH 1% aq. Suspension (Initial) | pH 1% aq. Suspension (14 days AHS) | % Imida ambient Initial | % imida at 54° C. 14 days | % imida degradation at 54° C. 14 days |
|---|---|---|---|---|---|
| 12 | 3.60 | 3.88 | 77.82 | 50.08 | 35.65 |

Thus Stability of Imidacloprid decreases with a decrease in pH.

As the stability decreases, the degradation increases.

1. Imidacloprid is stable at a pH of 5.90
2. Imidacloprid is unstable at a pH of 3.60 which may be obtained due to the presence of Citric acid in the ratio of 49.5:0.5 of Imidacloprid:Citric acid
3. Imidacloprid is still more unstable at a pH of 2.68 which may be obtained due to the presence of Citric acid in the ratio of 40:10 of Imidacloprid:citric acid.

It is further found that Imidacloprid is not stable in the presence of citric acid and moisture.

Experiment 13

Imidacloprid technical was taken from plant and mixed in laboratory mixer by adding 10 gm citric acid and 2 gm water and is then is kept in AHS stability study at 30, 45 and 54° C. in trilaminated pouches,

TABLE 31

Stability of Imidacloprid (40.0 gms) mixed with citric acid (10.0 gms) and with Water (2.0 gms) at 30° C.

| Expt. No. | pH 1% aq. Suspension (Initial) | pH 1% aq. Suspension (14 days AHS) | % Imida ambient Initial | % imida at 30° C. 14 days | % imida degradation at 30° C. 14 days |
|---|---|---|---|---|---|
| 13 | 2.70 | 4.8 | 74.61 | 12.57 | 83.15 |

TABLE 32

Stability of Imidacloprid (40.0 gms) mixed with citric acid (10.0 gms) and with Water (2.0 gms) at 45° C.

| Expt. No. | pH 1% aq. Suspension (Initial) | pH 1% aq. Suspension (14 days AHS) | % Imida ambient Initial | % imida at 45° C. 14 days | % imida degradation at 45° C. 14 days |
|---|---|---|---|---|---|
| 13 | 2.70 | 4.8 | 74.61 | 7.461 | 90.00 |

TABLE 33

Stability of Imidacloprid (40.0 gms) mixed with citric acid (10.0 gms) and with Water (2.0 gms) at 54° C.

| Expt. No. | pH 1% aq. Suspension (Initial) | pH 1% aq. Suspension (14 days AHS) | % Imida ambient Initial | % imida at 54° C. 14 days | % imida degradation at 54° C. 14 days |
|---|---|---|---|---|---|
| 13 | 2.70 | 4.8 | 74.61 | 3.73 | 95.19 |

Experiment 14

Imidacloprid technical was taken from the plant and mixed in laboratory mixer by adding 5 gm citric acid and 2 gm water and was then kept in AHS stability study at 30, 45 and 54° C. in trilaminated pouches.

TABLE 34

Stability of Imidacloprid (40.0 gms) mixed with citric acid (5.0 gms) and with Water (2.0 gms) at 30° C.

| Expt. No. | pH 1% aq. Suspension (Initial) | pH 1% aq. Suspension (14 days AHS) | % Imida ambient Initial | % imida at 30° C. 14 days | % imida degradation at 30° C. 14 days |
|---|---|---|---|---|---|
| 14 | 2.84 | 4.2 | 82.8 | 17.93 | 78.35 |

TABLE 35

Stability of Imidacloprid (40.0 gms) mixed with citric acid (5.0 gms) and with Water (2.0 gms) at 45° C.

| Expt. No. | pH 1% aq. Suspension (Initial) | pH 1% aq. Suspension (14 days AHS) | % Imida ambient Initial | % imida at 45° C. 14 days | % imida degradation at 45° C. 14 days |
|---|---|---|---|---|---|
| 14 | 2.84 | 4.2 | 82.8 | 8.69 | 89.51 |

TABLE 36

Stability of Imidacloprid (40.0 gms) mixed with citric acid (5.0 gms) and with Water (2.0 gms) at 54° C.

| Expt. No. | pH 1% aq. Suspension (Initial) | pH 1% aq. Suspension (14 days AHS) | % Imida ambient Initial | % imida at 54° C. 14 days | % imida degradation at 54° C. 14 days |
|---|---|---|---|---|---|
| 14 | 2.84 | 4.2 | 82.8 | 5.63 | 93.20 |

Thus Stability of Imidacloprid
a. Decreases with increase in the temperature
b. Decreases with a decrease in pH.
c. Decreases in the presence of moisture.
It is further found by experimentation that the combination product of Acephate+Imidacloprid which shows synergistic results is found to be unstable in the absence of coating.

Experiment 15

53 gm of Acephate technical was taken from the plant and mixed in a laboratory mixer by adding 3 gm imidacloprid without coating and without any citric acid. This was then kept in AHS stability study at 30, 45 and 54° C. in trilaminated pouches.

TABLE 37

Stability of Acephate + Imida (Uncoated) at 30° C.

| Expt. No. | pH 1% aq. Suspension (Initial) | pH 1% aq. Suspension (14 days AHS) | % Acephate ambient | % Acephate 30° C. 14 days | % Acephate Degradation 30° C. | % Imida ambient Initial | % imida at 30° C. 14 days | % imida degradation at 30° C. 14 days |
|---|---|---|---|---|---|---|---|---|
| 15 | 4.70 | 2.08 | 92.3 | 52.44 | 43.18 | 5.20 | 0.508 | 90.23 |

TABLE 38

Stability of Acephate + Imida (Uncoated) at 45° C.

| Expt. No. | pH 1% aq. Suspension (Initial) | pH 1% aq. Suspension (14 days AHS) | % Acephate ambient | % Acephate 45° C. 14 days | % Acephate Degradation 45° C. | % Imida ambient Initial | % imida at 45° C. 14 days | % imida degradation at 45° C. 14 days |
|---|---|---|---|---|---|---|---|---|
| 15 | 4.70 | 2.08 | 92.3 | 50.09 | 45.73 | 5.20 | 0.416 | 92..00 |

TABLE 39

Stability of Acephate + Imida (Uncoated) at 54° C.

| Expt. No. | pH 1% aq. Suspension (Initial) | pH 1% aq. Suspension (14 days AHS) | % Acephate ambient | % Acephate 54° C. 14 days | % Acephate Degradation 54° C. | % Imida ambient Initial | % imida at 54° C. 14 days | % imida degradation at 54° C. 14 days |
|---|---|---|---|---|---|---|---|---|
| 15 | 4.70 | 2.08 | 92.3 | 40.30 | 56.34 | 5.20 | 0.26 | 95.00 |

Experiment 16

53 gm of Acephate technical was taken from the plant and mixed in a laboratory mixer by adding 3 gm imidacloprid without encapsulation and with 2.2 gm of citric acid . This was then kept in AHS stability study at 30, 45 and 54° C. in trilaminated pouches.

TABLE 40

Stability of Acephate + Imida (Uncoated) mixed with Citric acid at 30° C.

| Expt. No. | pH 1% aq. Suspension (Initial) | pH 1% aq. Suspension (14 days AHS) | % Acephate ambient | % Acephate 30° C. 14 days | % Acephate Degradation 30° C. | % Imida ambient Initial | % imida at 30° C. 14 days | % imida degradation at 30° C. 14 days |
|---|---|---|---|---|---|---|---|---|
| 16 | 3.3 | 2.68 | 88.78 | 87.80 | 1.1 | 5.00 | 0.00 | 100 |

TABLE 41

Stability of Acephate + Imida (Uncoated) mixed with Citric acid at 45° C.

| Expt. No. | pH 1% aq. Suspension (Initial) | pH 1% aq. Suspension (14 days AHS) | % Acephate ambient | % Acephate 45° C. 14 days | % Acephate Degradation 45° C. | % Imida ambient Initial | % imida at 45° C. 14 days | % imida degradation at 45° C. 14 days |
|---|---|---|---|---|---|---|---|---|
| 16 | 3.3 | 2.68 | 88.78 | 87.62 | 1.3 | 5.00 | 0.00 | 100 |

TABLE 42

Stability of Acephate + Imida (Uncoated) mixed with Citric acid at 54° C.

| Expt. No. | pH 1% aq. Suspension (Initial) | pH 1% aq. Suspension (14 days AHS) | % Acephate ambient | % Acephate 54° C. 14 days | % Acephate Degradation 54° C. | % Imida ambient Initial | % imida at 54° C. 14 days | % imida degradation at 54° C. 14 days |
|---|---|---|---|---|---|---|---|---|
| 16 | 3.3 | 2.68 | 88.78 | 84.34 | 5.0 | 5.00 | 0.00 | 100 |

Therefore although the combination may exhibit synergy, it is not storage stable. A barrier is needed between the active ingredients of the combination as both the active ingredients have a tendency to degrade under different conditions of pH.

It is also a well known fact that conventional fillers used in a formulation like silica, kaolin have a tendency to absorb moisture from the atmosphere which in turn affects the pH leading to the degradation.

The composition of the present invention includes a barrier wall between the two active ingredients and has been found to provide improved storage stability in spite of the incompatability of the active ingredients.

The overall pH of the composition is between 3-4. Acephate has been found to be stable in a pH of 3-4 and degrades in alkaline pH. Since the overall pH of the composition is between 3-4 and Acephate is not expected to degrade whereas Imidacloprid has a tendency to degrade as evident from the results in Table H.

The improved storage stability of coated Imidacloprid by itself in the absence of Acephate due to the barrier coating is clear from the tables below

Experiment 17

In a laboratory plough shear mixture 291.5 gm of Imidacloprid of particle size ranging from 15 micron to 50 micron was charged and blended by operating only the plough. Then 204 gm PEG-8000 was heated in a separate vessel at 65° C. for 15 min. This heated PEG-8000 formed a transparent glassy liquid which was sprayed over Imidaclorpid technical previously charged in PSM using metering pump. After the complete spraying of the melted polymer the mixture was blended to form a homogeneous mass which was slowly cooled at room temp to obtain Imidacloprid coated with PEG-8000. This coated imidacloprid was tested for its accelerated storage stability 30, 45 and 54° C.

TABLE 43

Stability of coated Imidacloprid at 30° C.

| Expt. No. | pH 1% aq. Suspension (Initial) | pH 1% aq. Suspension (14 days AHS) | % Imida ambient Initial | % imida at 30° C. 14 days | % imida degradation at 30° C. 14 days |
|---|---|---|---|---|---|
| 17 | 5.8 | 4.3 | 57.13 | 57.13 | Nil |

TABLE 44

Stability of coated Imidacloprid at 45° C.

| Expt. No. | pH 1% aq. Suspension (Initial) | pH 1% aq. Suspension (14 days AHS) | % Imida ambient Initial | % imida at 45° C. 14 days | % imida degradation at 45° C. 14 days |
|---|---|---|---|---|---|
| 17 | 5.8 | 3.95 | 57.13 | 57.13 | Nil |

TABLE 45

Stability of coated Imidacloprid at 54° C.

| Expt. No. | pH 1% aq. Suspension (Initial) | pH 1% aq. Suspension (14 days AHS) | % Imida ambient Initial | % imida at 54° C. 14 days | % imida degradation at 54° C. 14 days |
|---|---|---|---|---|---|
| 17 | 5.8 | 3.21 | 57.13 | 57.13 | Nil |

Experiment 18

40 gm of above coated Imidacloprid technical and 10 gm of citric acid was mixed in a laboratory mixer and was then kept in AHS stability study at 30, 45 and 54° C. in trilaminated pouches.

TABLE 46

Stability of coated Imidacloprid mixed with Citric acid(10 gms) at 30° C.

| Expt. No. | pH 1% aq. Suspension (Initial) | pH 1% aq. Suspension (14 days AHS) | % Imida ambient Initial | % imida at 30° C. 14 days | % imida degradation at 30° C. 14 days |
|---|---|---|---|---|---|
| 18 | 2.70 | 2.82 | 45.20 | 45.20 | Nil |

TABLE 47

Stability of coated Imidacloprid mixed with Citric acid(10 gms) at 45° C.

| Expt. No. | pH 1% aq. Suspension (Initial) | pH 1% aq. Suspension (14 days AHS) | % Imida ambient Initial | % imida at 45° C. 14 days | % imida degradation at 45° C. 14 days |
|---|---|---|---|---|---|
| 18 | 2.7 | 2.85 | 45.20 | 45.20 | Nil |

TABLE 48

Stability of coated Imidacloprid mixed with Citric acid(10 gms) at 54° C.

| Expt. No. | pH 1% aq. Suspension (Initial) | pH 1% aq. Suspension (14 days AHS) | % Imida ambient Initial | % imida at 54° C. 14 days | % imida degradation at 54° C. 14 days |
|---|---|---|---|---|---|
| 18 | 2.71 | 2.98 | 45.20 | 41.50 | 8.18 |

Experiment 19

45 gm of above coated Imidacloprid technical and 05 gm of citric acid was mixed in a laboratory mixer and was then kept in AHS stability study at 30, 45 and 54° C. in trilaminated pouches.

TABLE 49

Stability of coated Imidacloprid(45 gms)mixed with Citric acid(5 gms) at 30° C.

| Expt. No. | pH 1% aq. Suspension (Initial) | pH 1% aq. Suspension (14 days AHS) | % Imida ambient Initial | % imida at 30° C. 14 days | % imida degradation at 30° C. 14 days |
|---|---|---|---|---|---|
| 19 | 2.86 | 2.99 | 51.30 | 51.30 | Nil |

TABLE 50

Stability of coated Imidacloprid (45 gms) mixed with Citric acid (5 gms) at 45° C.

| Expt. No. | pH 1% aq. Suspension (Initial) | pH 1% aq. Suspension (14 days AHS) | % Imida ambient Initial | % imida at 45° C. 14 days | % imida degradation at 45° C. 14 days |
|---|---|---|---|---|---|
| 19 | 2.86 | 3.01 | 51.30 | 50.90 | 0.78 |

TABLE 51

Stability of coated Imidacloprid (45 gms) mixed with Citric acid (5 gms) at 54° C.

| Expt. No. | pH 1% aq. Suspension (Initial) | pH 1% aq. Suspension (14 days AHS) | % Imida ambient Initial | % imida at 54° C. 14 days | % imida degradation at 54° C. 14 days |
|---|---|---|---|---|---|
| 19 | 2.86 | 3.45 | 51.30 | 50.30 | 1.95 |

Experiment 20

48 gm of above coated Imidacloprid technical and 02 gm of citric acid was mixed in laboratory mixer and was then kept in AHS stability study at 45 and 54° C. in trilaminated pouches.

TABLE 52

Stability of coated Imidacloprid (48 gm) mixed with Citric acid (2 gms) at 30° C.

| Expt. No. | pH 1% aq. Suspension (Initial) | pH 1% aq. Suspension (14 days AHS) | % Imida ambient Initial | % imida at 30° C. 14 days | % imida degradation at 30° C. 14 days |
|---|---|---|---|---|---|
| 20 | 3.56 | 3.58 | 55.10 | 55.10 | Nil |

TABLE 53

Stability of coated Imidacloprid (48 gm) mixed with Citric acid (2 gms) at 45° C.

| Expt. No. | pH 1% aq. Suspension (Initial) | pH 1% aq. Suspension (14 days AHS) | % Imida ambient Initial | % imida at 45° C. 14 days | % imida degradation at 45° C. 14 days |
|---|---|---|---|---|---|
| 20 | 3.56 | 4.01 | 55.10 | 54.18 | 1.66 |

TABLE 54

Stability of coated Imidacloprid (48 gm) mixed with Citric acid (2 gms) at 54° C.

| Expt. No. | pH 1% aq. Suspension (Initial) | pH 1% aq. Suspension (14 days AHS) | % Imida ambient Initial | % imida at 54° C. 14 days | % imida degradation at 54° C. 14 days |
|---|---|---|---|---|---|
| 20 | 3.56 | 4.23 | 55.10 | 54.20 | 1.633 |

Experiment 21

49.5 gm of above coated Imidacloprid technical and 0.5 gm of citric acid was mixed in laboratory mixer and was then kept in AHS stability study at 45 and 54° C. in trilaminated pouches.

TABLE 55

Stability of coated Imidacloprid (49.5 gms) mixed with Citric acid (0.5 gms) at 30° C.

| Expt. No. | pH 1% aq. Suspension (Initial) | pH 1% aq. Suspension (14 days AHS) | % Imida ambient Initial | % imida at 30° C. 14 days | % imida degradation at 30° C. 14 days |
|---|---|---|---|---|---|
| 21 | 4.10 | 4.15 | 56.5 | 56.5 | Nil |

TABLE 56

Stability of coated Imidacloprid (49.5 gms) mixed with Citric acid (0.5 gms) at 45° C.

| Expt. No. | pH 1% aq. Suspension (Initial) | pH 1% aq. Suspension (14 days AHS) | % Imida ambient Initial | % imida at 45° C. 14 days | % imida degradation at 45° C. 14 days |
|---|---|---|---|---|---|
| 21 | 4.10 | 4.45 | 56.5 | 55.91 | 1.04 |

TABLE 57

Stability of coated Imidacloprid (49.5 gms) mixed with Citric acid (0.5 gms) at 54° C.

| Expt. No. | pH 1% aq. Suspension (Initial) | pH 1% aq. Suspension (14 days AHS) | % Imida ambient Initial | % imida at 54° C. 14 days | % imida degradation at 54° C. 14 days |
|---|---|---|---|---|---|
| 21 | 4.10 | 4.55 | 56.5 | 55.87 | 1.11 |

It is clear from the experiments above that

1. Coated Imidacloprid is relatively stable at a pH of 4.10
2. Coated imidacloprid degrades by 1.95% at pH 2.83 at 54 deg
3. Coated Imidacloprid degrades still less by 1.63% at pH 3.12 at 54 deg
4. Coated Imidacloprid degrades very less by 1.1% at pH 3.63 at 54 deg Literature on the stability of imidacloprid has reported that Imidacloprid is stable at a pH of 5.60.

However, it was observed that when the Imidacloprid is coated, the synergistic composition of Imidacloprid and Acephate has been found to exhibit stability.

Experiment 22

53 gm of Acephate technical was taken from the plant and mixed in a laboratory mixer by adding 3 gm imidacloprid coated and 2.2 gm of citric acid. This was then kept in AHS stability study at 30, 45 and 54° C. in trilaminated pouches.

TABLE 58

Stability of Acephate + Imida (Coated) mixed with Citric acid at 30° C.

| Expt. No. | pH 1% aq. Suspension (Initial) | pH 1% aq. Suspension 14 days AHS | % Acephate ambient | % Acephate 30° C. 14 days | % Acephate Degradation 30° C. | % Imida ambient Initial | % imida at 30° C. 14 days | % imida degradation at 30° C. 14 days |
|---|---|---|---|---|---|---|---|---|
| 22 | 3.56 | 3.68 | 88.78 | 87.44 | 1.51 | 3.24 | 3.24 | Nil |

TABLE 59

Stability of Acephate + Imida (coated) mixed with Citric acid at 45° C.

| Expt. No. | pH 1% aq. Suspension (Initial) | pH 1% aq. Suspension 14 days AHS | % Acephate ambient | % Acephate 45° C. 14 days | % Acephate Degradation 45° C. | % Imida ambient Initial | % imida at 45° C. 14 days | % imida degradation at 45° C. 14 days |
|---|---|---|---|---|---|---|---|---|
| 22 | 3.56 | 3.68 | 88.78 | 87.18 | 1.80 | 3.24 | 3.21 | 0.93 |

TABLE 60

Stability of Acephate + Imida (coated) mixed with Citric acid at 54° C.

| Expt. No. | pH 1% aq. Suspension (Initial) | pH 1% aq. Suspension (14 days AHS) | % Acephate ambient | % Acephate 54° C. 14 days | % Acephate Degradation 54° C. | % Imida ambient Initial | % imida at 54° C. 14 days | % imida degradation at 54° C. 14 days |
|---|---|---|---|---|---|---|---|---|
| 22 | 3.56 | 3.68 | 88.78 | 86.56 | 2.485 | 3.24 | 3.201 | 1.203 |

The tables 39, 42 and 60 which provide information on the combination product show that 1. In the synergistic combination of Acephate+Imidacloprid uncoated, Acephate degrades by around 56% at 54° C. and imidacloprid degrades by 95% at 54° C. in the absence of Citric acid. (See table 39)
2. In the combination of Acephate+Imidacloprid uncoated and Citric acid, Acephate degrades by around 5% at 54° C. and imidacloprid degrades by 99.8% at 54° C. Thus the degradation of Acephate is reduced from 56% to 5% due to the presence of Citric acid. (See table 42)
3. In the synergistic combination of Acephate+Imidacloprid coated with Citric acid, Acephate degrades by around 2.48% at 54° C. and imidacloprid degrades by 1.23% at 54° C. (See table 60)

Thus it is clear that Acephate is most stable at a pH range of 3-4. Citric acid is added as a stabilizer to obtain the required pH range of 3-4. Similarly, it is clear that Imidacloprid is not stable under acidic pH. But the combination of Acephate and coated Imidacloprid is most stable at a pH range of 3-4; the pH being obtained due to the presence of citric acid. Whereas, the combination of Acephate and uncoated imidacloprid is not stable at a pH range of 3-4; the pH being obtained due to the presence of Citric acid.

The following examples of the composition are provided for illustrative purposes only and are not intended to limit the scope of the present invention. In these examples, percentage amounts refer to percent by weight unless otherwise noted

EXAMPLE 1

| INGREDIENT | WEIGHT (GM) |
|---|---|
| Acephate technical | 510.1 |
| Imidacloprid technical | 18.36 |
| Dispersol PS | 10.00 |
| Lissapol-D | 05.00 |
| Citric Acid | 10.00 |
| Precipitated Silica | 446.54 |
| TOTAL | 1000.00 g |

18.36 gm of Imidacloprid technical of particle size ranging from 15 micron to 50 micron was charged in a laboratory plough shear mixer. Acephate technical 510.1 gm along with 10 gm dispersol PS, 5 gm Lissapol D, 10 gm citric acid and 446.54 gm silica was charged in a laboratory ribbon blender and blended for 30 min to form homogeneous mass and blended for another hour to obtain the product (with uncoated Imidacloprid) of desired quality.

TABLE 61

Stability of Acephate and uncoated Imidacloprid at 45° C. after 14 days

| Example No. | % Acephate ambient | % Acephate 45° C. 14 days | % Acephate degraded | % Imida Ambient | % Imida 14 days @ 45° C. | % Imida degraded |
|---|---|---|---|---|---|---|
| 1 | 51.13 | 28.50 | 44.26 | 1.84 | 0.14 | 92.39 |

TABLE 62

Stability of Acephate and uncoated Imidacloprid at 54° C. after 14 days

| Example No. | % Acephate ambient | % Acephate 54° C. 14 days | % Acephate degraded | % Imida Ambient | % Imida 14 days @ 54° C. | % Imida degraded |
|---|---|---|---|---|---|---|
| 1 | 51.13 | 22.50 | 56.00 | 1.84 | 0.10 | 94.57 |

EXAMPLE 2

| INGREDIENT | WEIGHT (GM) |
|---|---|
| Acephate technical | 510.1 |
| Imidacloprid technical | 18.36 |
| PEG 8000 | 18.36 |
| Dispersol PS | 10.00 |
| Lissapol-D | 05.00 |
| Citric Acid | 10.00 |
| Precipitated Silica | 428.18 |
| TOTAL | 1000.00 g |

18.36 gm of Imidacloprid technical of particle size ranging from 15 micron to 50 micron was charged in a laboratory plough shear mixer. 18.36 gm PEG-8000 was heated in a separate vessel at 65° C. for 15 min. This formed a transparent glassy liquid which was sprayed over Imidacloprid technical previously charged in PSM using metering pump. After complete spraying of melted polymer the mixture was blended to form a homogeneous mass which was slowly cooled to room temp to obtain Imidacloprid coated with PEG-8000.

Acephate technical 510.1 gm along with 10 gm dispersol PS, 5 gm Lissapol D, 10 gm citric acid and 428.18 gm silica was charged in a laboratory ribbon blender and blended for 30 min to form homogeneous mass. 36.72 gm of coated Imidacloprid was added to this homogeneous mass and blended for another hour to obtain the product of desired quality.

EXAMPLE 3

| INGREDIENT | WEIGHT (GM) |
|---|---|
| Acephate technical | 510.1 |
| Imidacloprid technical | 18.36 |
| Ethoxylated Alcohol UNITHOX 480 | 18.36 |
| Dispersol PS | 10.00 |
| Lissapol-D | 05.00 |
| Citric Acid | 10.00 |
| Precipitated Silica | 428.18 |
| TOTAL | 1000.00 g |

18.36 gm of Imidacloprid of particle size ranging from 15 micron to 50 micron was charged in a laboratory plough shear mixture. 18.36 gm Unithox 480 was heated in a separate vessel at 65° C. for 15 min. This formed a transparent glassy liquid which was sprayed over Imidacloprid technical previously charged in PSM using metering pump. After complete spraying of melted polymer the mixture was blended to form homogeneous mass which was then slowly cooled at room temp to obtain Imidacloprid coated with Unithox 480.

Acephate technical 510.1 gm along with 10 gm dispersol PS 5 gm Lissapol D, 10 gm citric acid and 428.18 gm silica was charged in laboratory ribbon blender and blended for 25 min to form homogeneous mass. This mass was then mixed with coated imidacloprid in PSM to obtain desired quality product.

TABLE 63

Stability of Acephate and coated Imidacloprid at 45° C. after 14 days

| Example No. | % Acephate ambient | % Acephate 45° C. 14 days | % Acephate degraded | % Imida Ambient | % Imida 14 days @ 45° C. | % Imida degraded |
|---|---|---|---|---|---|---|
| 2 | 50.20 | 49.50 | 1.39 | 1.95 | 1.77 | 9.23 |

TABLE 64

Stability of Acephate and coated Imidacloprid at 54° C. after 14 days

| Example No. | % Acephate ambient | % Acephate 54° C. 14 days | % Acephate degraded | % Imida Ambient | % Imida 14 days @ 54° C. | % Imida degraded |
|---|---|---|---|---|---|---|
| 2 | 50.20 | 49.40 | 1.59 | 1.95 | 1.74 | 10.77 |

The above tables show that both Acephate as well as Imidacloprid remain stable when Imidacloprid is coated, the ratio of Imidacloprid and the coating material being in the ratio of 1:1

EXAMPLE 4

| INGREDIENT | WEIGHT (GM) |
|---|---|
| Acephate technical | 510.1 |
| Imidacloprid technical | 18.36 |
| PEG 8000 | 9.18 |
| Dispersol PS | 10.00 |
| Lissapol-D | 05.00 |
| Citric Acid | 10.00 |
| Precipitated Silica | 437.36 |
| TOTAL | 1000.00 g |

18.36 gm of Imidacloprid technical of particle size ranging from 15 micron to 50 micron was charged in a laboratory plough shear mixer. 9.18 gm PEG-8000 was heated in a separate vessel at 65° C. for 15 min. This heated PEG-8000 formed a transparent glassy liquid which was sprayed over Imidacloprid technical previously charged in PSM using metering pump. After complete spraying of melted polymer the mixture was blended to form a homogeneous mass. This mass was then slowly cooled at room temp to obtain Imidacloprid coated with PEG-8000. Acephate technical 510.1 gm along with 10 gm dispersol PS 5 gm Lissapol D, 10 gm citric acid and 437.36 gm silica was charged in laboratory ribbon blender charged and blended for 30 min to form homogeneous mass. 27.54 gm of coated Imidacloprid was added to the mass and blended for another hour to obtain the product of desired quality.

EXAMPLE 5

| INGREDIENT | WEIGHT (GM) |
| --- | --- |
| Acephate technical | 510.1 |
| Imidacloprid technical | 18.36 |
| Unithox 480 | 9.18 |
| Dispersol PS | 10.00 |
| Lissapol-D | 05.00 |
| Citric Acid | 10.00 |
| Precipitated Silica | 437.36 |
| TOTAL | 1000.00 g |

18.36 gm of Imidacloprid technical of particle size ranging from 15 micron to 50 micron was charged in a laboratory plough shear mixer. 9.18 gm Unithox 480 was heated in a separate vessel at 65° C. for 15 min. This heated Unithox 480 formed a transparent glassy liquid which was sprayed over Imidacloprid technical previously charged in PSM using metering pump. After complete spraying of melted polymer the mixture was blended to form a homogeneous mass. This mass was then slowly cooled at room temp to obtain Imidacloprid coated with Unithox 480. Acephate technical 510.1 gm along with 10 gm dispersol PS 5 gm Lissapol D, 10 gm citric acid and 437.36 gm silica was charged in laboratory ribbon blender charged and blended for 30 min to form homogeneous mass. 27.54 gm of coated Imidacloprid was added to the mass and blended for another hour to obtain the product of desired quality.

TABLE 65

Stability of Acephate and coated Imidacloprid at 45° C. after 14 days

| Example No. | % Acephate ambient | % Acephate 45° C. 14 days | % Acephate degraded at 45° C. 14 days | % Imida Ambient | % Imida 14 days@ 45° C. | % Imida degraded |
| --- | --- | --- | --- | --- | --- | --- |
| 4 | 50.59 | 48.90 | 3.34 | 2.0 | 1.65 | 17.5 |

TABLE 66

Stability of Acephate and coated Imidacloprid at 54° C. after 14 days

| Example No. | % Acephate ambient | % Acephate 54° C. 14 days | % Acephate degraded 54° C. 14 days | % Imida Ambient | % Imida 14 days@ 54° C. | % Imida degraded |
| --- | --- | --- | --- | --- | --- | --- |
| 5 | 50.59 | 48.49 | 4.15 | 2.0 | 1.65 | 17.5 |

The above tables show that both Acephate as well as Imidacloprid remain stable when Imidacloprid is coated, the ratio of Imidacloprid and the coating material being in the ratio of 2:1

EXAMPLE 6

| INGREDIENT | WEIGHT (GM) |
| --- | --- |
| Acephate technical | 510.1 |
| Imidacloprid technical | 18.36 |
| PEG 8000 | 36.72 |
| Dispersol PS | 10.00 |
| Lissapol-D | 05.00 |
| Citric Acid | 10.00 |
| Precipitated Silica | 409.82 |
| TOTAL | 1000.00 g |

18.36 gm of Imidacloprid technical of particle size ranging from 15 micron to 50 micron was charged in a laboratory plough shear mixer. 36.72 gm PEG-8000 was heated in a separate vessel at 65° C. for 15 min. This formed a transparent glassy liquid which was sprayed over Imidacloprid technical previously charged in PSM using metering pump. After complete spraying of melted polymer the mixture was blended to form a homogeneous mass which was slowly cooled to room temp to obtain Imidacloprid coated with PEG-8000.

Acephate technical 510.1 gm along with 10 gm dispersal PS 5 gm Lissapol D, 10 gm citric acid and 409.82 gm silica was charged in a laboratory ribbon blender and blended for 30 min to form homogeneous mass. 55.08 gm of coated Imidacloprid was added to this homogeneous mass and blended for another hour to obtain the product of desired quality.

EXAMPLE 7

| INGREDIENT | WEIGHT (GM) |
| --- | --- |
| Acephate technical | 510.1 |
| Imidacloprid technical | 18.36 |
| Ethoxylated Alcohol UNITHOX 480 | 36.72 |
| Dispersol PS | 10.00 |
| Lissapol-D | 05.00 |
| Citric Acid | 10.00 |
| Precipitated Silica | 409.82 |
| TOTAL | 1000.00 g |

18.36 gm of Imidacloprid of particle size ranging from 15 micron to 50 micron was charged in a laboratory plough shear mixture. 36.72 gm Unithox 480 was heated in a separate vessel at 65° C. for 15 min. This formed a transparent glassy liquid which was sprayed over Imidacloprid technical previously charged in PSM using metering pump. After complete spraying of melted polymer the mixture was blended to form homogeneous mass which was then slowly cooled at room temp to obtain Imidacloprid coated with Unithox 480.

Acephate technical 510.1 gm along with 10 gm dispersol PS 5 gm Lissapol D, 10 gm citric acid and 409.28 gm silica was charged in laboratory ribbon blender and blended for 25 min to form homogeneous mass. This mass was then mixed with 55.08 gm coated imidacloprid in PSM to obtain desired quality product.

TABLE 67

Stability of Acephate and coated Imidacloprid at 45° C. after 14 days

| Example No. | % Acephate ambient | % Acephate 45° C. 14 days | % Acephate degraded | % Imida Ambient | % Imida 14 days @ 45° C. | % Imida degraded |
| --- | --- | --- | --- | --- | --- | --- |
| 6 | 50.25 | 49.85 | 0.80 | 1.98 | 1.83 | 7.58 |

TABLE 68

Stability of Acephate and coated Imidacloprid at 54° C. after 14 days

| Example No. | % Acephate ambient | % Acephate 54° C. 14 days | % Acephate degraded | % Imida Ambient | % Imida 14 days @ 45° C. | % Imida degraded |
| --- | --- | --- | --- | --- | --- | --- |
| 6 | 50.25 | 48.60 | 3.28 | 1.98 | 1.8 | 8.08 |

The above tables show that both Acephate as well as Imidacloprid remain stable when Imidacloprid is coated, the ratio of Imidacloprid and the coating material being in the ratio of 1:2

EXAMPLE 8

| INGREDIENT | WEIGHT (GM) |
|---|---|
| Acephate technical | 510.1 |
| Imidacloprid technical | 18.36 |
| PEG 8000 | 55.08 |
| Dispersol PS | 10.00 |
| Lissapol-D | 05.00 |
| Citric Acid | 10.00 |
| Precipitated Silica | 391.46 |
| TOTAL | 1000.00 g |

18.36 gm of Imidacloprid technical of particle size ranging from 15 micron to 50 micron was charged in a laboratory plough shear mixer. 55.08 gm PEG-8000 was heated in a separate vessel at 65° C. for 15 min. This formed a transparent glassy liquid which was sprayed over Imidacloprid technical previously charged in PSM using metering pump. After complete spraying of melted polymer the mixture was blended to form a homogeneous mass which was slowly cooled to room temp to obtain Imidacloprid coated with PEG-8000.

Acephate technical 510.1 gm along with 10 gm dispersol PS 5 gm Lissapol D, 10 gm citric acid and 391.46 gm silica was charged in a laboratory ribbon blender and blended for 30 min to form homogeneous mass. 73.44 gm of coated Imidacloprid was added to this homogeneous mass and blended for another hour to obtain the product of desired quality.

EXAMPLE 9

| INGREDIENT | WEIGHT (GM) |
|---|---|
| Acephate technical | 510.1 |
| Imidacloprid technical | 18.36 |
| Ethoxylated Alcohol UNITHOX 480 | 55.08 |
| Dispersol PS | 10.00 |
| Lissapol-D | 05.00 |
| Citric Acid | 10.00 |
| Precipitated Silica | 391.46 |
| TOTAL | 1000.00 g |

18.36 gm of Imidacloprid of particle size ranging from 15 micron to 50 micron was charged in a laboratory plough shear mixture. 55.08 gm Unithox 480 was heated in a separate vessel at 65° C. for 15 min. This formed a transparent glassy liquid which was sprayed over Imidacloprid technical previously charged in PSM using metering pump. After complete spraying of melted polymer the mixture was blended to form homogeneous mass which was then slowly cooled at room temp to obtain Imidacloprid coated with Unithox 480.

Acephate technical 510.1 gm along with 10 gm dispersol PS 5 gm Lissapol D, 10 gm citric acid and 391.46 gm silica was charged in laboratory ribbon blender and blended for 25 min to form homogeneous mass. This mass was then mixed with 73.44 gm coated imidacloprid in PSM to obtain desired quality product.

TABLE 69

Stability of Acephate and coated Imidacloprid at 45° C. after 14 days

| Example No. | % Acephate ambient | % Acephate 45° C. 14 days | % Acephate degraded | % Imida Ambient | % Imida 14 days@ 45° C. | % Imida degraded |
|---|---|---|---|---|---|---|
| 8 | 50.21 | 50.00 | 0.42 | 1.93 | 1.88 | 2.59 |

TABLE 70

Stability of Acephate and coated Imidacloprid at 54° C. after 14 days

| Example No. | % Acephate ambient | % Acephate 54° C. 14 days | % Acephate degraded | % Imida Ambient | % Imida 14 days@ 54° C. | % Imida degraded |
|---|---|---|---|---|---|---|
| 7 | 50.21 | 49.92 | 0.58 | 1.93 | 1.85 | 4.15 |

The above tables show that both Acephate as well as Imidacloprid remain stable when Imidacloprid is coated, the ratio of Imidacloprid and the coating material being in the ratio of 1:3

Although the present invention has been disclosed in terms of a preferred embodiment, it will be understood that numerous additional modifications and variations could be made thereto without departing from the scope of the invention as defined by the following claims.

We claim:

1. An improved storage stable formulation for the protection of crops comprising as active ingredients imidacloprid and acephate, wherein imidacloprid is provided with a coating of a water soluble polymer in melt form and said formulation further includes a pH stabilizer that provides an overall pH of the formulation between 3-4.

2. The improved storage stable formulation as claimed in claims 1 further comprising wetting agents, dispersing agents, and inert fillers.

3. The improved storage stable formulation as claimed in claim 1 comprising (i) imidacloprid in an amount in the range of 0.1-25 wt % of the total weight of the formulation, (ii) acephate in an amount in the range of 5-97 wt % of the total weight of the formulation and (iii) a coating of a water soluble polymer in an amount in the range of 0.08-50 wt % of the total weight of the formulation.

4. The improved storage stable formulation as claimed in claim 3 further comprising (iv) a wetting agent in an amount in the range of 0.1-2.0 wt % of the total weight of the formulation, (v) a dispersing agent in an amount in the range of 0.5-7.0 wt % of the total weight of the formulation, and (vi) inert fillers in an amount in the range of 10-50 wt % of the total weight of the formulation.

5. The improved storage stable formulation as claimed in claim 1 wherein the water soluble polymer is selected from the group consisting of PEG 4000, PEG 6000, PEG 8000, PEG 10000, polyacrylamide, sodium polyacrylate, and copolymer of methyl methacrylate, butyl methacrylate and dimethylaminoethyl methacrylate.

6. The improved storage stable formulation as claimed in claim 3 wherein the water soluble polymer is selected from the group consisting of PEG 4000, PEG 6000, PEG 8000, PEG 10000, polyacrylamide, sodium polyacrylate, and copolymer of methyl methacrylate, butyl methacrylate and dimethylaminoethyl methacrylate.

7. The improved storage stable formulation as claimed in claim 4 wherein the water soluble polymer is selected from the group consisting of PEG 4000, PEG 6000, PEG 8000, PEG 10000, polyacrylamide, sodium polyacrylate, and copolymer of methyl methacrylate, butyl methacrylate and dimethylaminoethyl methacrylate.

8. A process for the preparation of an improved storage stable formulation for the protection of crops comprising,
   a) providing as active ingredients imidacloprid and acephate;
   b) coating imidacloprid with a water soluble polymer in melt form;
   c) providing a pH stabilizer that imparts an overall pH of the formulation between 3-4;
   d) blending the ingredients to form a homogenous mixture in powder form; and
   e) optionally, converting the powder into granules or pellets.

9. The process of claim 8, wherein the water soluble polymer is selected from the group consisting of PEG 4000, PEG 6000, PEG 8000, PEG 10000, polyacrylamide, sodium polyacrylate, and copolymer of methyl methacrylate, butyl methacrylate and dimethylaminoethyl methacrylate.

10. The process of claim 8, wherein imidacloprid is present in an amount in the range of 0.1-25 wt % of the total weight of the formulation, acephate is present in an amount in the range of 5-97 wt % of the total weight of the formulation and the water soluble polymer is present in an amount in the range of 0.08-50 wt % of the total weight of the formulation.

11. The improved storage stable formulation of claim 1, wherein said pH stabilizer is citric acid.

12. The process of claim 8, wherein said pH stabilizer is citric acid.

* * * * *